United States Patent

Brown, Jr., deceased et al.

Patent Number: 6,084,242
Date of Patent: Jul. 4, 2000

[54] METHOD AND DEVICE FOR STIMULATING THE IMMUNE SYSTEM AND GENERATING HEALING AT THE CELLULAR LEVEL

[76] Inventors: Doyle S. Brown, Jr., deceased, late of Deltona, Fla.; Mary R. Brown, executor, 1163 E. Swanson Dr., Deltona, Fla. 32738

[21] Appl. No.: 09/110,349

[22] Filed: Jul. 6, 1998

[51] Int. Cl.[7] .................................................. A61N 5/06

[52] U.S. Cl. .................. 250/504 R; 250/495.1; 606/3; 607/88; 607/89

[58] Field of Search ......................... 250/504 R, 504 H, 250/495.1; 607/88, 89; 606/3

[56] References Cited

U.S. PATENT DOCUMENTS

| | | | |
|---|---|---|---|
| 4,686,986 | 8/1987 | Fenyo et al. | 250/504 R |
| 4,930,504 | 6/1990 | Diamantopoulos et al. | 250/504 H |
| 5,196,004 | 3/1993 | Sinofsky | 606/3 |
| 5,755,752 | 5/1998 | Segal | 607/89 |

*Primary Examiner*—Jack Berman
*Attorney, Agent, or Firm*—Arthur G. Yeager

[57] ABSTRACT

A method and device for stimulating the immune system employs a laser diode to provide a source of infrared radiation with a wavelength around 1917 nm through a tube or guide to the skin of a patient near an ailment or other infirmity such as a disease to be treated. Control circuitry for pulsing the beam at a rate of 7.5 hz is provided.

25 Claims, 3 Drawing Sheets

METHOD AND DEVICE FOR STIMULATING THE IMMUNE SYSTEM AND GENERATING HEALING AT THE CELLULAR LEVEL

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

The present invention is directed towards the use of electromagnetic radiation to heal and treat various ailments including cancer, particularly to the use of a non-laser beam of infrared radiation.

2. Description of the Related Art

A wide variety of uses of infrared radiation, whether laser or non-laser, to treat various medical ailments are known in the art. Most of the art involves either therapeutic heating of tissue or laser-oriented removal of tissue. Other uses of radiation involve thermal coagulation of blood and similar applications. The use of chemical agents in immuno-therapy is also well known. What is needed is a low power infrared device and method to stimulate the immune system to promote normal and expedited healing and to generate healing at the cellular level without harm to normal tissue.

BRIEF SUMMARY OF THE INVENTION

In one aspect of the present invention there is provided a method of assisting the healing of various human infirmities by generating healing at the cellular level comprising the steps of: locating a source of electromagnetic radiation adjacent a surface of a human body and adjacent a location of an infirmity; and operating the source at a predetermined level to stimulate the immune system without significant effect on normal cells of the body. The method includes the step of: directing infrared radiation. Other steps include directing infrared radiation having a wavelength of approximately 1917 nm; pulsing the radiation applied at a rate of 7.5 hz; and directing radiation in the form of a non-coherent radiation beam. The method also includes the step of: directing infrared radiation having a wavelength in the range of approximately 1800–2400 nm. Further aspects of the invention include the steps of: creating infrared radiation from a laser source; and directing the radiation through a guide before directing the radiation onto the surface of the body. An additional step includes locating the source at a second location on the surface of the body separated away from a location adjacent an infirmity for stimulating the immune system at the second location.

In other aspects of the present invention there is provided a device for stimulating the human immune system to assist in the healing of an ailment comprising first means for generating electromagnetic radiation and second means for directing the radiation onto the surface of a body adjacent the location of an ailment to be healed. The first means includes circuit means for generating infrared radiation. The circuit means includes laser diode circuit means for generating a beam of infrared radiation. The second means includes guide means for directing the beam onto the surface of a body.

In other aspects of the invention the first means includes infrared radiation generating means for generating radiation at a wavelength of approximately 1800–2040 nm. The radiation is generated to have a power peak at a wavelength of approximately 1917 nm. Additionally, the first means includes pulse control means to generate the radiation at a selectable pulse rate. The pulse rate is approximately 7.5 hz.

In a final aspect of the present invention there is provided a device for stimulating the human immune system to assist in the healing of an ailment comprising first means for generating a beam of infrared radiation having a wavelength of approximately 1917 nm, control circuit means for selectively controlling the rate at which the beam is generated by the first means.

BRIEF DESCRIPTION OF THE SEVERAL VIEWS OF THE DRAWING

The novel features which are believed to be characteristic of this invention are set forth with particularity in the appended claims. The invention itself, however, both as to its organization and method of operation, together with further objects and advantages thereof, may best be understood by reference to the following description taken in connection with the accompanying drawings, in which:

DETAILED DESCRIPTION OF THE INVENTION

Figure 1:
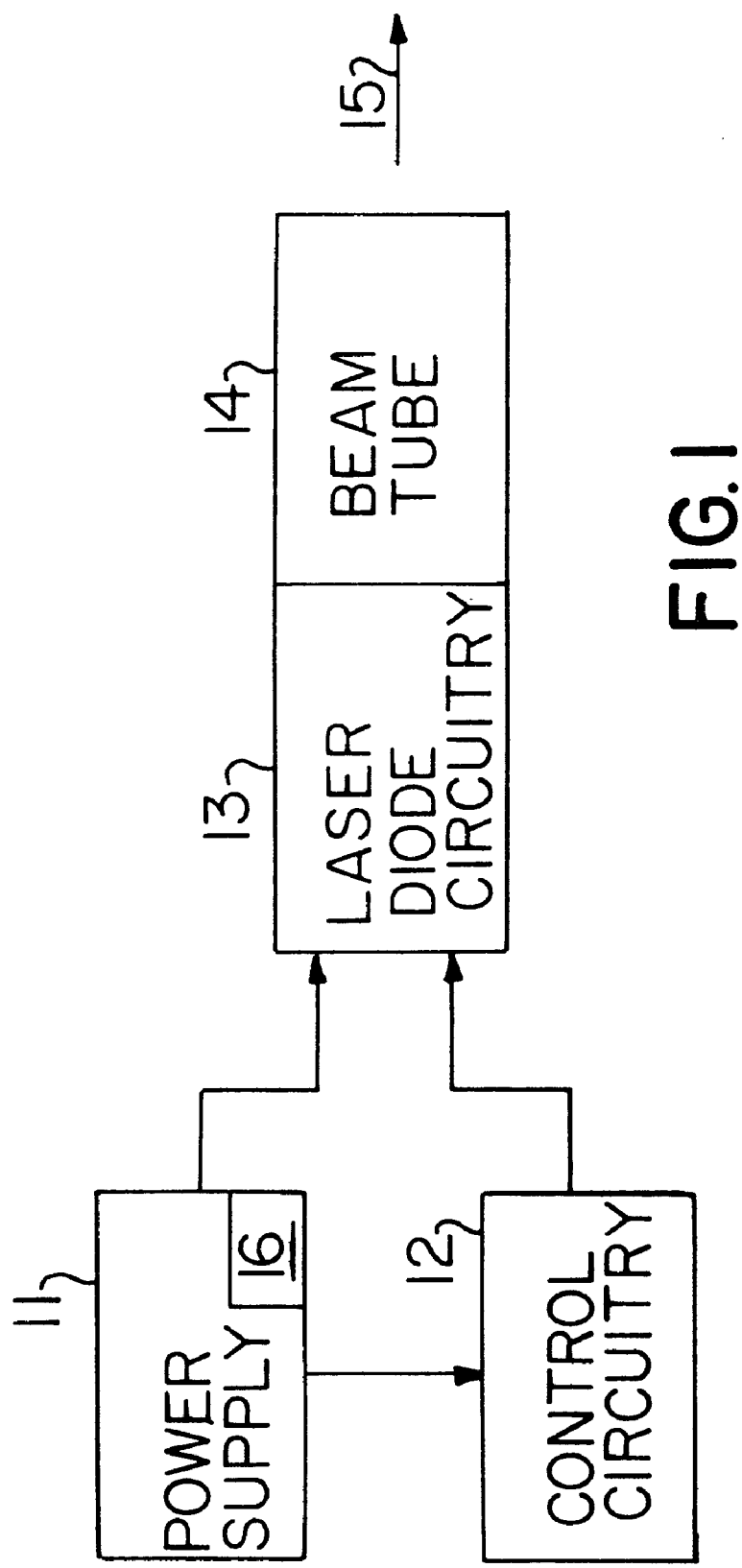
FIG. 1 is a functional block diagram of the components of the device in accord with the present invention.
Figure 2:
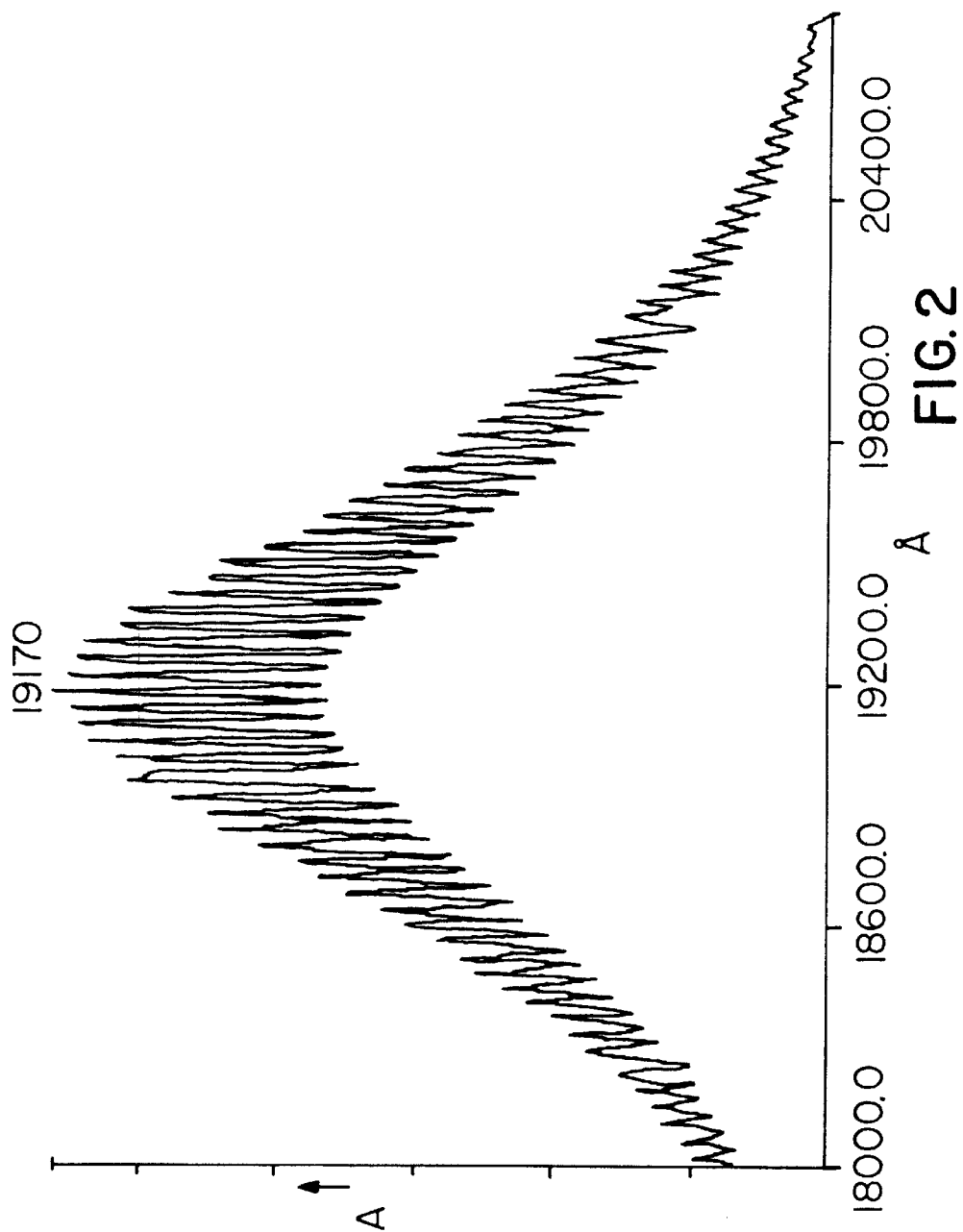
FIG. 2 is a graph of the signal strength and frequency for the infrared beam created by the present invention.

With reference to the drawings, a low power radiation device is shown generally at 10 in FIG. 1. Power supply 11 provides electric power to a control unit 12 and a laser diode circuit 13. Circuit 13 preferably provides an output beam of 1917 nm with a 50% power bandwidth of 126 nm as illustrated in FIG. 2. The laser beam emerges from beam tube 14 as beam 15. The tube 14 has a diameter of one inch. The control unit 12 provides for pulsed operation of diode circuitry 13 at a rate that is preferably 7.5 hz with a power output that is at least 10 mw. Beam 15 is about ⅜ inch in diameter. The system is energized via conventional switch 16.

Beam 15 is not "coherent radiation" as the phrase is used with respect to laser technology but is derived from a laser source via circuitry 13. If the present invention is used in a straight laser mode a 30 degree beam spread is recommended. In addition, the usual safety procedures, particularly with regard to eye protection, must be followed.

A pulse rate of 7.5 hz is recommended. Any rate from cw to any frequency can be used, but negative psychological side effects, such as depression or lethargy, below 7.5 hz and nervousness, headaches, to extreme agitation above 7.5 hz, may occur for some people.

OPERATION OF THE SYSTEM

When an area of the body is treated with the beam 15 there will be an effect on the entire body due to the stimulation of the immune and circulatory systems. For example, when a subject is treated for a viral infection, the areas treated are the sinuses, throat, neck and chest area. Treatment times usually are 30 to 60 seconds on the chest, 15 to 20 seconds on the throat and 20 seconds for the sinuses. Thus the lymphatic system is stimulated in the eradication of the virus. If the viral infection is treated at the onset of the first symptoms, the subject usually runs a very low-grade fever for one or two hours following the treatment and within six to eight hours all adverse symptoms normally disappear. If a treatment is given after the symptoms have progressed, the treatment alleviates the symptoms and shortens the cycle of the flu or cold.

When the device 10 is used to treat a localized cancer, the beam 15 is focused externally on the area (3.5 minutes for adenocarcinoma of the prostate). Not only is the area stimulated but also the immune system including the T-cells. To further enhance the healing process, the bones of the arms and legs (front-external) are treated to stimulate the bone marrow production of the B cells. The device 10 can be adjusted if necessary to carry a power output of up to 200 mw to treat very difficult afflictions, such as bone cancer and leukemia. Such increased power would minimize the number of treatments necessary versus using the low power mode of the unit 10. With the present device 10, depending on the extent of the infirmity, and the condition of the individual's immune system, positive results have been achieved in as little as one treatment. The device 10 has produced positive results in individuals with an impaired immune system having a T-cell count of under 4 (normal being 20.0–51.1) and with CD4/CD8 ratio of 0.1 (normal being 1.0–3.4).

With inflammatory infirmities such as arthritis and impact injuries where swelling is a concern, immediate results are achieved with one external treatment to the afflicted area. The swelling will visibly recede as the treatment is administered. Bruising is eliminated if the treatment with device 10 is given soon after impact. Results are achieved anywhere from immediate treatment to several hours later for such infirmities. The device 10 may be used for treatment after dental procedures and after surgery (both medical and cosmetic) to promote healing and minimize swelling and bruising.

The device 10 and beam 15 are eye-safe. No eye protection is needed. The eyes can be treated for infections, stys and impact injuries and other applications.

Figure 3:
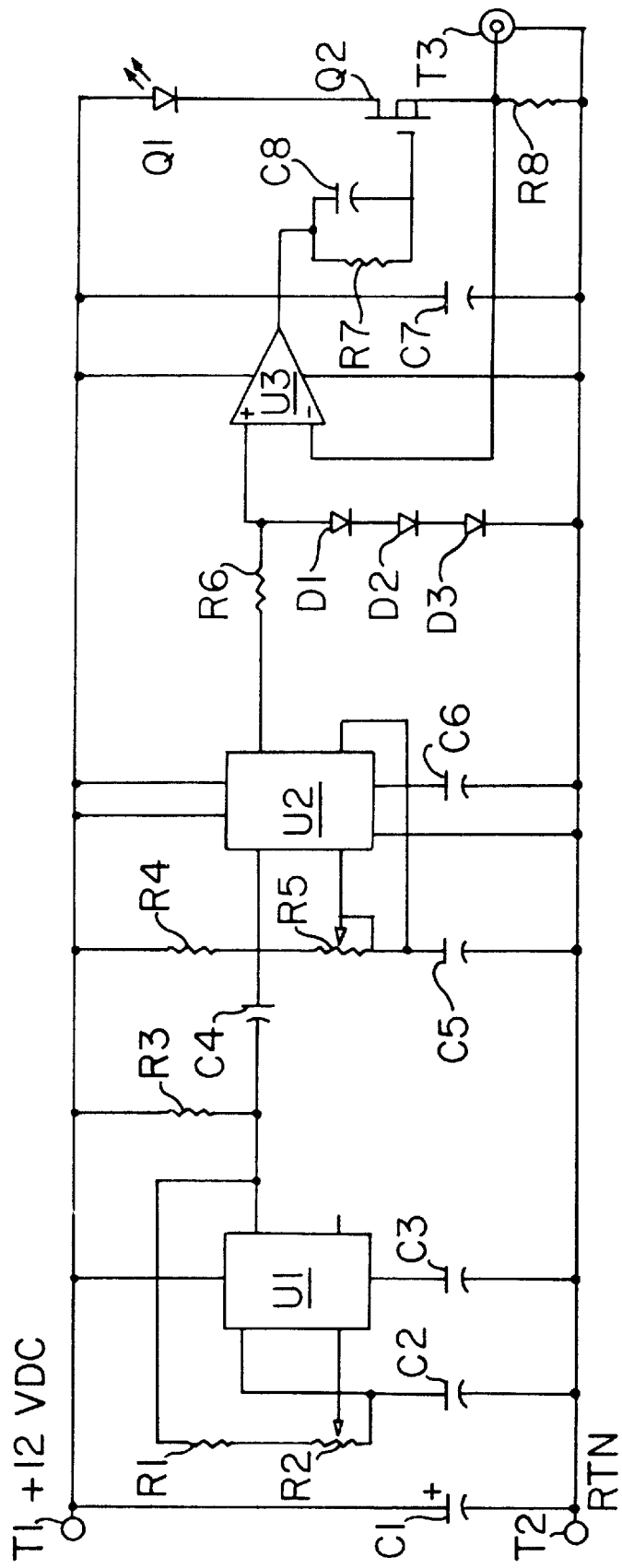
FIG. 3 is a simplified schematic diagram of the control circuitry of FIG. 1.

FIG. 3 illustrates a simplified schematic diagram of the system. A basic oscillator is formed by one half of the dual timing circuit made of U1 and U2. It is configured as a free running astable multivibrator. The frequency is set by R2. The most desirable oscillator frequency has been established by testing and is 7.5 hz.

Output of the oscillator is applied to the trigger input of the second half of the timing circuit which is configured as a monostable multivibrator or commonly known as a (one shot) pulse generator. A series of pulses are thus generated repeating every 133 milliseconds (7.5 hz) with a pulse duration of approximately 25 milliseconds which is set by the 200K ohm potentiometer. This pulse train output drives the next section which is designed to maintain a constant current in the laser diode, Q1, for the duration of each pulse. The on to off time ratio (known as duty cycle) is about 20%.

By pulsing the positive input to the operational amplifier U3 high, a voltage is developed across the three forward biased diodes D1–D3 and this voltage (approximately 2.1 volts) is used as the reference voltage to set the laser diode current and is applied to the positive input to U3. If the positive input is higher than the negative input, the output will go high and stay high until the voltage at the negative input becomes equal to the reference voltage at the positive input. U3 can control the current flowing through Q1 by either increasing or decreasing the voltage at the gate of the N channel field effect transistor Q2 which causes a change in the internal resistance of the FET. By changing the resistance of Q2 from the source to the drain, the current flow in Q1 is changed. This current is sampled by developing a feedback voltage across R8 that is in the drain to ground of the FET. The feedback voltage is applied to the negative input of U3. When the feedback voltage becomes equal to the reference voltage the current in the FET will stop increasing and becomes fixed. This action allows U3 to hold the current constant or regulate the current in Q2 and Q1. The voltage can be measured at jack T3.

Once the current is regulated, the voltage across Q1 is not critical and will seek its own level, varying with temperature and the duty cycle of the device. A constant current of approximately 2 amps is established by the reference voltage and is not adjustable. Q2 is conducting the same current in Q1 and with a 12 volt DC source from power supply 11 connected at T1 and T2 will dissipate approximately 2.25 watts. A heat sink is required to prevent Q2 from overheating. The heat generated in Q1 is about ⅓ that of Q2. The large heat sink used is not so much to dissipate the excess heat, but to keep Q1 at a constant temperature in order to maintain infrared light output at the desired wavelength. All laser diodes exhibit a frequency shift with temperature change. The most suitable wavelength has been established by testing and produces the therapeutic effect desired.

The metal tube or guide 14 surrounding the laser diode output from circuitry 13 is used to concentrate the beam 15 into an area the size of the tube diameter on the surface of the skin being treated. This is accomplished by the polished surface on the inner wall of the tube, used to reflect the beam 15 back into the area being irradiated instead of spreading out on the surrounding surface.

Resistors R1–R8, capacitors C1–C8, diodes D1–D3, and Q1 and Q2 are all standard components used as understood in the art.

The following data was developed from treatments of subjects with the device 10.

EXAMPLES

CANCER

Example 1 Subject: Ovarian Tumor-female age 29 Grapefruit size malignant tumor diagnosed by her physician. 2 days later; 15 minute treatment with device 10.
Next day; Subject called. Said that she had putrid brown vaginal discharge.
3 days later; Subject called. Said vaginal discharge stopped.
2 days later; Subject called. Said she returned to physician the day before. Tumor was gone and she tested negative for cancer.
18 months later; Spoke with subject. She had quarterly checkups. Now having semi-annual checkups. No indication of recurrence. She remains negative for cancer.
Example 2: Subject: Breast Tumor-Female age 24 3 small malignant tumors approximately 1 cm in diameter, diagnosed by her physician.
Four days later; 10 minute treatment with device 10.
7 days later; Subject returned to physician and after reexamination, it was determined that the tumors were gone.
Example 3: Subject: Breast Tumor-female age 26 2 malignant tumors approximately 1 cm and 1.5 cm in diameter diagnosed by her physician.

2 days later: 5 minute treatment with device 10.
5 days later: Subject reported after reexamination by her physician. It was determined the tumors were gone.
8 months later: Subject reported no recurrences.
Example 4: Subject: Ovarian Tumor-female age 23 Malignant ovarian tumor approximately 7 cm in diameter diagnosed by her physician.
3 days later: 5 minute treatment with device 10.
4 days later: Subject reported reexamination by her physician revealed the tumor was no longer there. Other tests were run.
4 days later: Subject reported that other tests for cancer were negative.
6 months later: Subject reported no recurrence at this date.
16 months later: Subject reported no recurrence at this date.
Example 5: Subject: Cancer of lymph gland-male age 36 Cancer of the lymph gland starting in upper neck on left side & spreading to upper torso left side. Diagnosed by his physician.
4 days later: 10 minute treatment with device 10.
4 days later: Subject was reexamined by his physician and was told that his cancer was in remission.
2 weeks later: Subject reported he had been reexamined and retested by his physician and was told that he no longer had cancer.
26 months later: Subject is having semi-annual checkups. He has tested negative for cancer.
Example 6: Subject: Brain tumor-female age 45 Malignant brain tumor causing increasingly severe headaches, diagnosed by her physician.
Three weeks later: 5 minute treatment with device 10.
Next day: Subject reported that the headaches stopped.
Next day: 5 minute treatment with device 10. Subject no longer taking pain medication.
9 days later: Subject retested by her physician and told her tumor was in remission.
16 days later: Subject retested by her physician and told that she had total remission of her brain tumor. All tests negative for cancer.
Example 7: Subject: Lung Cancer-male age 52 Malignant, fast growing tumor in left lung-has not metastasized. Diagnosed by his physician.
3 days later: 5 minute treatment with device 10.
5 days later: Subject reported examination by his physician on previous day had revealed the tumor was in remission.
Next day: Subject reported examination by his physician on previous day had revealed the tumor was in remission.
Next day: 5 minute treatment with device 10.
5 days later: Subject reported examination by physician determined the tumor was 20% the size of the original tumor.
1 week later: Subject reported examination by physician revealed the tumor was gone. Other tests were run.
4 days later: Subject reported all tests for cancer were negative.
19 months later: Talked to subject. He is having regular checkups and has had no recurrence of cancer.
Example 8: Subject: Skin Cancer-female age 88 Squamous cell carcinoma upper right side of back and senile keratosis 4 inch area behind right ear. Diagnosed by her physician.
Next day: 5 minute treatment in each area with device 10.
Next day: 5 minute treatment in each area with device 10. Observed remission.
Next day: 5 minute treatment in each area with device 10. Observed remission.
4 days later: Examination by her physician revealed squamous cell carcinoma in complete remission and senile keratosis 70% remission.
2 weeks later: Examination by her physician-full remission in both areas.
Example 9: Subject: Prostate Cancer-male age 56 Malignant prostate tumor, possible metastasis, diagnosed by his physician.
3 days later: 5 minute treatment with device 10.
2 days later: 5 minute treatment with device 10.
9 days later: Examination by his physician revealed complete remission of prostate tumor and no metastasis.
22 months later: No recurrence to this date.
Example 10: Subject: Cancer of the Pancreas-male age 50 Malignant pancreatic tumors diagnosed by his physician.
3 days later: 10 minute treatment with device 10.
3 days later: 10 minute treatment with device 10. Pain subsided the day before.
8 days later: Examination by his physician determined complete remission of tumors.
3 days later: Other test results negative for cancer.
Example 11: Subject: Rectal Cancer-male age 57 Malignant tumor of the rectum diagnosed by his physician.
4 days later: 5 minute treatment with device 10.
2 days later: 5 minute treatment with device 10.
8 days later: Examination by his physician detected complete remission of tumor.
4 days later: Other tests negative for cancer.
16 days later: Tests negative for cancer.
1 month later: Tests negative for cancer.
1 month later: Tests negative for cancer.

ARTHRITIS

Example 12: Subject: Rheumatoid Arthritis-male age 39 Rheumatoid arthritis mid. joint second finger, right hand. Diagnosed by his physician. Pain and swelling getting progressively worse. No deformity of the joint, yet.
6 months later: 5 minute treatment with device 10.
Next day: Subject called & said that the pain was gone and about 90% of the swelling was gone.
Next day: Subject called and said that all of the swelling was gone.
6 months later: Spoke with Subject. No recurrence to this date.
17 months later: Spoke with Subject. No recurrence to this date.
18 months later: Spoke with Subject. No recurrence to this date.
19 months later: Spoke with Subject. No recurrence to this date.
Example 13: Subject: Osteoarthritis-female age 43 Osteoarthritis right hip, diagnosed by her physician. Pain getting progressively worse. Worse at the end of the day.
6 days later: 5 minute treatment with device 10.
2 days later: Subject reported that the pain was much less. Still worse at the end of the day, but not as bad.
Next day: 5 minute treatment with device 10.
4 days later: Subject reported no pain except at the end of the day.
1 week later: Subject reported no pain except at the end of a strenuous day.
2 weeks later: Subject reported no pain. Hip completely mobile.
5 weeks later: Subject reported no recurrence of pain or stiffness.
20 months later: Subject reported no recurrence of pain or stiffness.
18 months later: Subject reported no recurrence of pain or stiffness.
Example 14: Subject: Osteoarthritis-female age 86 Osteoarthritis lower back caused by injury 6 years earlier. Diagnosed by her physician.

9 weeks later: 10 minute treatment with device 10.
Next day: Subject reported pain almost gone.
Next day: 10 minute treatment with device 10.
2 days later: Subject reported no more pain.
15 months later: Subject reported no recurrence of pain.
10 months later: Subject reported no recurrence of pain.
Example 15: Subject: Osteoarthritis-male age 56 Osteoarthritis right knee. Diagnosed by his physician.
2 days later: 5 minute treatment with device 10.
3 days later: Subject reported about 80% remission of pain.
Next day: 5 minute treatment with device 10.
3 days later: Reported 100% remission of pain. Full mobility of knee joint.
6 weeks later: Subject reported no recurrence of pain or stiffness.

CARPAL TUNNEL SYNDROME & ARTHRITIS

Example 16: Subject: Carpal Tunnel Syndrome-female age 88 Carpal tunnel syndrome affecting both thumbs. Diagnosed by her physician. Subject says that the pain is getting progressively worse. Knitting is especially painful. She is to the point that 30 minutes of knitting produces such severe pain that she is forced to stop.
9 weeks later: 5 minute treatment with device 10.
Next day: Subject reported pain almost gone.
Next day: 5 minute treatment with device 10.
4 days later: Subject reported pain was completely gone.
9 days later: Subject reported she was able to knit 6½ hours in one day with no pain or discomfort.
10 months later: Subject reported no recurrence of pain or discomfort.
7 months later: Subject reported no recurrence of pain or discomfort.
Example 17: Subject: Rheumatoid Arthritis-male age 43. Rheumatoid arthritis finger joints and wrist, both hands. Diagnosed by his physician. Pain & swelling of finger joints & pain in wrist. No deformity of the joints, yet.
3 months later: 5 minute treatment each hand & wrist with device 10.
Next day: Subject reported pain completely gone. Swelling almost gone.
Next day: Subject reported pain completely gone. Swelling completely gone.
6 months later: Subject reported no recurrence.
6 months later: Subject reported no recurrence.

ADHESIVE CAPSULITIS

Example 18: Subject: Adhesive Capsulitis-female age 42 Adhesive capsulitis right shoulder diagnosed by her physician. Subject experienced severe pain of right shoulder & restriction of movement of right arm.
2 days later: 10 minute treatment of right shoulder area and upper portion of right arm with device 10.
Next day: Subject reported significant reduction of pain and some improvement in mobility of right arm.
4 days later: 10 minute treatment of right shoulder area and upper portion of right arm with device 10. Subject reported further reduction of pain and increased mobility of right arm.
1 week later: Subject reported no pain and further improvement in mobility of right arm.
2 months later: Subject reported no pain and full mobility of right arm.
2 months later: Subject reported no recurrence.
Example 19: Subject: Stroke victim-female age 87 Stroke victim diagnosed be her physician with a cataract in each eye. Removal of cataract from left eye scheduled.
3 months later: Cerebral embolis-left occipital lobe infarction diagnosed by her doctor. Diagnosis: Blind for life. Had first treatment with device 10. Vision started to return after the first treatment. Three more treatments, one per day for the next three (3) days.
8 days later: Re-examined by her physician after the stroke when the vision returned following the treatments. Cataract surgery was re-scheduled.
3 weeks later: Scan of left eye and surgery scheduled.
3 weeks later: Successful cataract surgery on left eye.
10 months later: Second cataract extraction on right eye.
Example 20: Subject: 55 year old male diagnosed by his doctors with prostate cancer-adenocarcinoma/DJD degenerative joint disease/hemorrhoids in a one month period.
About 5–6 weeks later: After 3 treatments with device 10 the hemorrhoids were gone. Almost no pain in areas diagnosed with DJD, with long periods of no pain at all. There was no swelling. No pain medication after the first treatment. All symptoms from the prostate cancer have been eliminated. No pressure pain, no dripping, no up to the bathroom during the night to urinate. The urination flow had increased and subject was able to fully empty his bladder. Sex drive and energy returned.
1–4 weeks later: Continued with treatments and status continued as above. The urination flow increased again. Subject is scheduled to be retested.
Example 21: Subject: Osteoarthritis-male age 39 Osteoarthritis diagnosed by his physician.
1 day to 2 weeks later: Six treatments with device 10. Pain/symptoms are gone. Continues with one treatment every six months.
Example 22: Subject: Inguinovulvar Gland Infection-female age 44 Inguinovulvar gland infection which occurs every month since age 15. Diagnosed by her doctor. Diagnosed by her doctor with perineal acne.
About 3 months later: Diagnosed by her doctor with inguinovulvar sebaceous gland infection. Prescribed bactroban. Approximately 4 years later: A series of eight (8) treatments with device 10. Gradual decrease in the number, size and duration of the outbreaks. No breakouts in areas where repetitive breakouts occurred monthly since age 15. Subject continues now with one (1) treatment per month. Also had treatments on both hands for swelling and pain and the treatments corrected both problems.
In addition the subject also had treatments on her sinuses for congestion and pain and both symptoms disappeared.
Example 23: Subject: Male age 26 Had arthoscopic surgery on right knee. Horseshoe shaped tear in cartilage was removed. Since surgery, experienced occasional pain in right knee and also left knee. Had several treatments on both knees. Pain and swelling disappeared.
6 years later: Was bitten on inside of left foot by unknown spider type. Quarter sized blister appeared. Was given antibiotic for spider bite by his doctor. Several days later, blister unchanged. Reexamined and blister was drained and subject was given stronger antibiotic by his doctor. Blister reappeared several days later. Had treatment with device 10.
One day later, blister is gone.
Example 24: Subject: Genital Herpes-female age 32 Genital herpes diagnosed by her physician. Has already had one outbreak.
Two treatments with the device 10. Began treatment on the second breakout. After the first treatment the lesions healed quickly. The second treatment was given for the third breakout. This outbreak was much milder than the other two. These lesions healed much faster than the others.
Two years later: No further treatments have been given. There have been no more outbreaks even under periods of severe stress.

Example 25: Inflammation, bruising, pain, circulation, cold and flu virus, hemorrhoids.

Several subjects had treatments with the device 10 for common, everyday occurrences. Areas of inflammation had immediate permanent relief. Bruising was eliminated except where beam 15 was unable to penetrate due to a metal object. Pain was alleviated and/or eliminated. Healing was hastened. Cold and flu viruses, if caught in the early stages, were eradicated from the body in ¼ of the normal time. Immediately after treatment for a virus, a very low grade fever will ensue and within 12 to 24 hours all symptoms are gone. Hemorrhoids substantially shrank and were not causing problems for the subjects after two treatments with device 10.

The present method is believed to be far superior to any technique currently in use for the treatment of cancer. The absence of any negative side effects is also very significant. The brief duration of the treatment, the low number of treatments required, and the fact that the treatment can be done in the physician's office, indicate that this method will be much more economical than any currently in use. The same can be said of a variety of arthritic conditions treated with the present method.

Although not completely understood, it is believed that the treatment with beam 15 (the healing or "H ray") stimulates the healing cells causing cuts, incisions, bruises, etc. to heal much faster than normal. It also is believed to stimulate the immune system causing infections to heal at a faster rate. In cases where immune cells are malfunctioning, such as rheumatoid arthritis, multiple sclerosis, muscular dystrophy, etc., the treatment is believed to return the cells to normal, causing them to stop attacking healthy cells.

It appears that the healing that transpires at the point of contact with the beam 15 takes place within the epidermis and the dermis. A sublayer of the epidermis is the stratum corneum which contains keratin, and the lower level where the melanocyte cells are found that produce the pigment. The dermis, located under the epidermis is where the pain and touch receptors are located. These receptors reach to the surface of the skin. Also in the dermis are the blood vessels that supply the nutrition to the skin. With a treatment by device 10, a person can feel warmth and or tingling, sometimes a pulling or tugging sensation such as on a cut and coolness on an infected area. This appears to be the explanation of why the beam 15 heals bruises, keeps skin young and supple, lessens scarring and promotes fast healing of soft tissue injuries. For example, if part of a bruised area is covered with foil and then the beam 15 treatment is administered, only the part not covered will not bruise. The covered part turns the usual purple, green and yellow and takes days to go away.

Overall, it is believed that the treatment has a very positive effect on nonmutated cells and a lethal effect on cancer cells.

Testing done recently with the device 10 gives indications that the positive effect of the device 10 can be blocked by cortisone and other steroids, chemotherapy and radiation therapy, and conventional treatments for AIDS.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by letters patent of the united states is:

1. A device for stimulating the human immune system to assist in the healing of an ailment comprising a single laser diode for generating a beam of infrared radiation having a wavelength of approximately 1917 nm and control circuit means for selectively controlling the rate at which said beam is generated by said diode.

2. The device as defined in claim 1 wherein said means includes tube means for directing said radiation in a form of a beam onto surface of a body.

3. The device as defined in claim 1 wherein said control circuit means is selectable to provide a pulse rate of approximately 7.5 hz.

4. The device as defined in claim 1 wherein radiation is generated to have a 50% power bandwidth of 126 nm.

5. The device as defined in claim 1 wherein said circuit means for generating infrared radiation provides infrared radiation at a power level of approximately 10 mw to 200 mw.

6. A method of assisting the healing of various human infirmities comprising the steps of:
   A. positioning and directing a single source of infrared electromagnetic radiation having a wavelength of approximately 1917 nm from a laser diode adjacent a surface of a human body and adjacent a location of an infirmity; and
   B. operating the source to provide the radiation of Step A onto a surface of a human body at a predetermined level to stimulate the immune system without significant effect on normal cells of the body.

7. The method of claim 6 wherein step B includes the step of:
   C. selecting the radiation power level to be at least 10 mw.

8. The method of claim 6 wherein step A includes the step of:
   C. directing the radiation through a tube before providing the radiation onto the surface of a body in step B.

9. A method of assisting the healing of various human infirmities comprising the steps of:
   A. positioning and directing a single source of infrared electromagnetic radiation from a laser diode adjacent a surface of a human body and adjacent a location of an infirmity; and
   B. operating the source to pulse the radiation of step A at a rate of 7.5 hz onto a surface of a human body at a predetermined level to stimulate the immune system without significant effect on normal cells of the body.

10. The method of claim 9 wherein step B includes the step of:
    C. selecting the radiation power level to be at least 10 mw.

11. The method of claim 9 wherein step A includes the step of:
    C. directing infrared radiation having a wavelength in the range of approximately 1800–2040 nm.

12. The method of claim 9 wherein step A includes the step of:
    C. directing the radiation through a tube before providing the radiation onto the surface of a body in step B.

13. A method of assisting the healing of various human infirmities comprising the steps of:
    A. positioning and directing a single source of infrared electromagnetic radiation in the form of a non-coherent radiation beam from a laser diode adjacent a surface of a human body and adjacent a location of an infirmity; and
    B. operating the source to provide the radiation of Step A onto a surface of a human body at a predetermined level to stimulate the immune system without significant effect on normal cells of the body.

14. The method of claim 13 wherein step B includes the step of:

C. selecting the radiation power level to be at least 10 mw.

15. The method of claim 13 wherein step A includes the step of:

C. directing infrared radiation having a wavelength in the range of approximately 1800–2040 nm.

16. The method of claim 13 wherein step A includes the step of:

C. directing the radiation through a tube before providing the radiation onto the surface of a body in step B.

17. A method of assisting the healing of various human infirmities comprising the steps of:

A. positioning a single source of infrared electromagnetic radiation from a laser diode adjacent a surface of a human body and adjacent a location of an infirmity;

B. operating the source to provide the radiation of Step A onto a surface of a human body at a predetermined level to stimulate the immune system without significant effect on normal cells of the body; and C. locating the single source at a second location for directing the radiation on a surface of a body remote from an infirmity for stimulating the immune system at the second location.

18. The method of claim 17 wherein step B includes the step of:

D. selecting the radiation power level to be at least 10 mw.

19. The method of claim 17 wherein step A includes the step of:

D. directing infrared radiation having a wavelength in the range of approximately 1800–2040 nm.

20. The method of claim 17 wherein step A includes the step of:

D. directing the radiation through a tube before directing the radiation onto the surface of a body in step B.

21. A device for stimulating the human immune system to assist in the healing of an ailment comprising a single laser diode circuit generating infrared electromagnetic radiation from a single source and means for directing said radiation onto the surface of a body adjacent the location of an ailment to be healed, said first means including pulse control means to generate said radiation at a selectable pulse rate, said pulse control means being selectable to provide a pulse rate of approximately 7.5 hz.

22. The device as defined in claim 21 wherein said means for directing includes tube means for directing said radiation in the form of a beam onto a surface of a body.

23. The device as defined in claim 21 wherein said radiation is generated to have a power peak at a wavelength of approximately 1917 nm.

24. The device as defined in claim 21 wherein said circuit includes infrared radiation generating means for generating radiation at a wavelength of 19917 and a 50% power bandwidth of 126 nm.

25. The device as defined in claim 21 wherein said circuit for generating infrared radiation provides infrared radiation at a power level of 10 mw or greater.

* * * * *